United States Patent [19]

Galperin et al.

[11] Patent Number: 5,440,034
[45] Date of Patent: Aug. 8, 1995

[54] METHOD OF PREPARING AZACYCLOHEPTANES

[75] Inventors: Leonid B. Galperin, Wilmette; Jeffrey C. Bricker, Buffalo Grove, both of Ill.

[73] Assignee: UOP, Des Plaines, Ill.

[21] Appl. No.: 174,093

[22] Filed: Dec. 28, 1993

[51] Int. Cl.⁶ .......................................... C07D 223/04
[52] U.S. Cl. ................................................ 540/612
[58] Field of Search ...................................... 540/612

[56] References Cited
U.S. PATENT DOCUMENTS 3,903,079  9/1975  Heinz et al. ....................... 540/612

OTHER PUBLICATIONS

S. M. Csicsery, *Ind. Eng. Chem. Proc. Des. Dev.*, 18, 191 (1979).
J. A. Weiszmann, "Handbook of Petroleum Refining Processes", R. A. Meyers, ed., McGraw-Hill Book Company, 1986, pp. 3–8.
N. Y. Chen and T. Y. Yan, *Ind. Eng. Chem. Proc. Des. Dev.*, 25, 151 (1986).

*Primary Examiner*—John M. Ford
*Attorney, Agent, or Firm*—Thomas K. McBride; Eugene I. Snyder

[57] ABSTRACT

Propylamines are dehydrocyclized by non-acidic molecular sieves containing a Group VIII zerovalent metal to afford azacycloheptanes with good selectivity. The molecular sieves show less than 5% activity in a standard heptene-1 isomerization test. Performing the reaction in the presence of hydrogen and/or ammonia often is beneficial.

17 Claims, No Drawings

METHOD OF PREPARING AZACYCLOHEPTANES

BACKGROUND OF THE INVENTION

Dehydrocyclization as a unit process has held a prominent place in the petroleum refining industry for some time. Quite broadly the process encompasses the conversion of $C_2$-$C_{12}$ olefins and paraffins to aromatics and naphthenes, but the process can be divided into two segments on both chemical mechanistic grounds and refinery operational considerations. In one branch light paraffins and/or olefins in the $C_2$-$C_5$ range are converted to naphthenes and aromatics, necessarily of higher carbon number, by a sequence of reactions including dehydrogenation, dimerization and oligomerization of olefins, and cyclization. Typically the process is referred to as dehydrocyclodimerization, which clearly indicates the various component processes occurring. See S. M. Csicsery, *Ind. Eng. Chem. Proc. Des. Dev.*, 18, 191 (1979). In another branch olefins and/or paraffins of 6 or more carbon numbers are converted to naphthenes and aromatics of the same carbon number or less. It is this last branch which is of greatest interest to us here.

The dehydrocyclization of paraffins to naphthenes and aromatics is a difficult reaction, limited by an equilibrium which shifts somewhat toward cyclization as the molecular weight (i.e., chain length) of the paraffin increases. Dehydrocyclization is favored by low pressures and high temperatures and may be catalyzed by, e.g., dual functional catalysts having both metal and acid functions. See J. A. Weiszmann, "Handbook of Petroleum Refining Processes", R. A. Meyers, ed., McGraw-Hill Book Company, 1986, page 3–8. Two types of catalysts have been identified for dehydrocyclization of paraffins; dual functional catalysts as described above and monofunctional catalysts possessing no significant acidity. The latter class of catalysts generally contains platinum on a neutral or a basing support, and includes such materials as platinum on a zeolite where all of the zeolitic activity has been removed by exchange with alkali or alkaline earth metal cations such as potassium sodium, barium, and so forth. More recently, N. Y. Chen and T. Y. Yan, *Ind. Eng. Chem. Proc. Des. Dev.*, 25, 151 (1986) have distinguished between two mechanistic routes for the aromatization of light hydrocarbons based on studies performed with n-hexane. One reaction path is a more or less direct road from the paraffin to aromatics, largely benzene, as effected over such catalysts as $Pt/Al_2O_3$, $Cr_2O_3/Al_2O_3$, $CoMo/Al_2O_3$ and $Te/NaY$. The other mechanistic route involves a pathway toward cracked intermediates which subsequently react to afford aromatics. The latter is said to be characteristic of HZSM-5 as catalyst and can be recognized by a spectrum of $C_6$-$C_{10}$ aromatics in the product stream from n-hexane.

While exploring dehydrocyclization under a range of conditions we pondered the possibility of using amines as a feedstock instead of the paraffins normally used. Various reactions can be contemplated, and without a hint from the prior art as to appropriate catalysts or probable reaction products we performed a general survey. In this application we report on our results on the dehydrocyclization of propylamines. In particular, we have found that under appropriate reaction conditions one can prepare azacycloheptanes from secondary and tertiary propylamines. Since the seven-membered nitrogen heterocycle is otherwise difficult to prepare, especially in large commercial quantities, our new synthesis provides a valuable entry into the family of azacycloheptanes.

SUMMARY OF THE INVENTION

The purpose of our invention is to prepare azacycloheptanes by dehydrocyclization of propylamines. An embodiment comprises the dehydrocyclization of secondary or tertiary propylamines over a dehydrocyclization catalyst of a Group VIII zerovalent metal impregnated on a non-acidic molecular sieve, where the reaction occurs at 250°–600° C., optionally in the presence of hydrogen or ammonia. In a more specific embodiment the catalyst is a potassium-exchanged zeolite L containing platinum. In another embodiment the amine is di-n-propylamine. In yet another embodiment the amine is tri-n-propylamine. Other embodiments and variants will be clear from the ensuing description.

DESCRIPTION OF THE INVENTION

We have observed that secondary and tertiary amines having propyl and substituted propyl groups attached to the nitrogen undergo dehydrocyclization at dehydrocyclization conditions to afford azacycloheptane. This reaction appears unprecedented and affords an unexpected entry into the seven-membered nitrogen-containing heterocyclic series. The synthesis can be effected by non-acidic molecular sieves impregnated with one or more Group VIII metals, especially platinum, and is of broad applicability as a preparative method.

The feedstocks of our invention are secondary and tertiary propylamines of the general formula

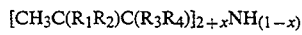

where $x=0$ or 1, corresponding to a secondary and tertiary amine, respectively. It needs to be explicitly understood that although it is the secondary and tertiary amines which undergo the dehydrocyclization reactions to form azacycloheptanes, under reaction conditions primary amines are converted, in part, to secondary amines which then can undergo the claimed reaction. Thus feedstocks of primary amines also may be used, but with the recognition that dehydrocyclization occurs only with the secondary and/or tertiary amines formed from the primary amines.

Each of $R_1$ and $R_2$ is independently selected from the group consisting of hydrogen and methyl. Each of $R_3$ and $R_4$ in the foregoing formula is independently selected from the group consisting of hydrogen, methyl, and ethyl. Examples of amines which may be used in the practice of our invention include di-n-propylamine ($R_1=R_2=R_3=R_4=H$, $x=0$), tri-n-propylamine ($R_1=R_2=R_3=R_4=H$ and $x=1$), di-s-butylamine ($R_1=R_2=R_3=H$, $R_4=CH_3$), tri-s-butylamine, di-i-butylamine ($R_1=CH_3$, $R_2=R_3=R_4=H$), tri-i-butylamine di-(3-pentyl)amine ($R_1=R_2=R_3=H$, $R_4=$ethyl), tri-(3-pentyl)amine, di-(3-methyl-2-butyl)amine ($R_1=R_3=H$, $R_2=R_4=$methyl), di-(1,1-dimethyl-1-propyl)amine ($R_1=R_2=H$, $R_3=R_4=$methyl), tri(1,1-dimethyl-1-propyl)amine, and so forth.

Also encompassed within our invention are feedstocks of unsymmetrical secondary and tertiary propyl amines as exemplified by n-propyl-s-butylamine, $(CH_3CH_2CH_2)NH(CH(CH_3)CH_2CH_3)$, di-(n-propyl)-s-butylamine, $(CH_3CH_2CH_2)_2N(CH(CH_3)CH_2CH_3)$, n-propyl-s-butyl-i-butylamine, (CH₃CH₂CH₂)N(CH(CH₃)CH₂CH₃)(CH₂CH)CH₃)₂), and so forth.

Dehydrocyclization of the foregoing amines to the corresponding azacycloheptanes may be effected using as a catalyst a non-acidic molecular sieve impregnated with a Group VIII zerovalent metal so long as the sieve pore size can accommodate the amine and azacycloheptanes of this invention. Among the molecular sieves which may be used in the practice of this invention are included zeolite L, zeolite Y, mordenite, zeolite beta, SAPO-5, SAPO-37, ALPO-5, MgAPSO-31, and the class of molecular sieves commonly referred to as "MFI". This class contains high silica aluminosilicates whose framework topology is represented by ZSM-5 and silicalite and having a silica/alumina ratio of at least 20. See *Atlas of Zeolite Structure Types*; W. M. Meier and D. H. Olson, Butterworths (London), 1987. Zeolite L is preferred in the practice of our invention.

By "non-acidic" molecular sieves is meant that the hydrogen cation of the molecular sieve is exchanged with a metal cation, usually that of an alkali or alkaline earth metal, although other suitable cations may be used such as those of the lanthanide series, as exemplified by lanthanum, cerium, samarium, dysprosium, and so forth, and metal cations such as those from zinc. The primary alkali metals, which form Group IA of the Periodic Table, are sodium, potassium, and lithium. Potassium is the most favored alkali metal for exchange with sodium being the next favored metal. Among the alkaline earth (Group IIA of the Periodic Table) metals barium and magnesium are preferred. Substantially complete exchange (i.e., at least 99%) of the hydrogen cation by one or more metal cations is the most desirable variant, although exchange of at least 95% of the exchangeable hydrogen cations is often sufficient.

Operationally, a suitable catalyst also may be defined as one which exhibits 0–5% activity in the heptene test, which is a measure of catalyst activity in the isomerization of heptene. In particular, a catalyst suitable for use in our invention will effect not more than 5% skeletal isomerization of heptene-1 at 425° C. using a gas flow of 250 cc per minute and 250 mg. catalyst at a hydrogen:-heptene-1 molar ratio of 40 at 1 atmosphere pressure. See the example for further details.

The alkali or alkaline earth metal exchanged molecular sieves of our invention also contain at least one Group VIII zerovalent metal, which includes iron, cobalt, nickel, ruthenium, rhodium, palladium, osmium, iridium, platinum, and all combinations thereof, with platinum being preferred. Such metals are deposited on the molecular sieve by impregnation of the sieve with a suitable salt of the metal, generally from an aqueous solution, followed by reduction of the metal cation to its zerovalent state. Suitable procedures are well known to one of ordinary skill in the catalyst art and need not be further elaborated upon. The amount of Group VIII metal on the dehydrocyclization catalyst may be as little as about 0.05 weight percent and may be as great as 20 weight percent, depending upon the metal, with the range between about 0.1 and 1.0 weight percent preferred in the practice of this invention for metals such as platinum and palladium.

The feedstocks of our invention are dehydrocyclized in the presence of a Group VIII impregnated alkali or alkaline earth metal exchanged molecular sieve under dehydrocyclization conditions. Dehydrocyclization conditions span a modest range and include a temperature between about 250 up to about 600° C., with the range between about 350° and 500° C. being favored. Reaction may be conducted at modest pressures from atmospheric up to about 500 psig, although it is preferred that the reaction be conducted at pressures in the range up to about 100 psig. Dehydrocyclization also may be performed in the presence of hydrogen, which serves to stabilize the catalyst against coking (which deactivates the catalyst), and/or in the presence of ammonia, which serves to minimize amine decomposition such as 2 $RNH_2 \rightarrow RNHR + NH_3$ When hydrogen is employed it may be used in an amount from 0.2 up to 10 molar proportions based on amines in the feedstock. When used, ammonia most often is from 0.1 up to 1.0 molar proportions based on amines in the feedstock.

Although the reaction may be conducted in either a batch or continuous process we prefer to carry out our invention in a continuous mode. In this variant of our invention a fixed bed of catalyst is favored, although an ebullating bed, a fluidized bed, or a radial bed also are suitable variants. A flowing stream of the reactant amines of our invention, either as pure components or in solution using a suitable organic solvent which is otherwise inert under reaction conditions, is passed over the dehydrocyclization catalysts of our invention at reaction conditions. As previously mentioned, the catalysts are alkali or alkaline metal exchanged molecular sieve impregnated with at least one Group VIII zerovalent metal. Reaction conditions include a pressure from atmospheric up to about 500 psig, preferably up to 100 psig, and a temperature from about 250° up to about 600° C. The reaction can be optionally carried out in the presence of either hydrogen and/or ammonia. Where hydrogen is present its concentration ranges between about 0.2 up to about 10 molar proportions relative to amines in the feedstock, and where ammonia is present its concentration ranges between about 0.1 up to about 1 molar proportion relative to the amines of the feedstock.

The following example illustrates the synthesis of azacycloheptane according to the process of our invention. This example is only illustrative and is not meant to limit our invention in any way.

EXAMPLE 1

Acidity by Isomerization Activity: Heptene Test. A microreactor was loaded with 250 mg of the catalyst to be tested, and a test mixture containing hydrogen and heptene-1 at a molar ratio of 40:1 was flowed over the catalyst at 425° C., 1 atmosphere pressure, at rates of 62.5, 125, 250, and 500 cc per minute. Effluent was analyzed for extent of skeletal isomerization. Using gamma alumina as a catalyst there was ca. 85% conversion to isomerized product at 250 cc per minute, whereas there was no measurable conversion when potassium-exchanged zeolite L was the catalyst.

EXAMPLE 2

Dehydrocyclization of Di-n-propylamine. Catalyst (10 cc of 0.8% platinum on zeolite-L exchanged with potassium so as to contain 14.2 weight percent potassium) was loaded into a ⅜" tube reactor and heated to 350° C. in a flowing stream of hydrogen (27 cc/min). The feedstock of di-n-propylamine was injected into the reactor at a rate of 10 cc/hour in the presence of ammonia injected at the rate of 27 cc/min. The reaction products were collected in a dry ice trap and yield of liquid product was 68.5 weight percent. Amine conversion and product selectivity were determined from the following formulae.

Conversion = 100%-(concentration of
di-n-propylamine in product)×(% yield of liquid)
Selectivity = (weight fraction) of component in
product×(% yield of liquid product)/Conversion Results are summarized in Table 1. When the reaction was conducted at 450° C. the yield of liquid product was 78.9%.

TABLE 1

| Conversion of Dipropylamine to Azacycloheptane[a] | | | | | |
|---|---|---|---|---|---|
| T, °C. | | | 350° C. | | 450° C. |
| Amine Conversion, wt % | 81.7 | 76.0 | 65.5 | 42.3 | 98.4 |
| % Selectivity to Azacycloheptane | 13.2 | 33.9 | 17.6 | 44.0 | 8.1 |
| % Selectivity to Alkylpyridines | 3.0 | 8.8 | 7.0 | 1.7 | 21.0 |
| % Selectivity to Propane Selectivity | 10.9 | 7.2 | 28.9 | 8.1 | 7.3 |
| % Selectivity to Propionitrile | 11.6 | 1.8 | 5.3 | 0.2 | 34.9 |
| $H_2$:HC[b] | 1 | — | — | 1 | 1 |
| $NH_3$:HC[c] | 1 | — | 1 | — | 1 |

[a]LHSV of pure di-n-propylamine was 1 hr$^{-1}$; atmospheric pressure.
[b]Molar ratio hydrogen to di-n-propylamine.
[c]Molar ratio ammonia to di-n-propylamine.

EXAMPLE 3

Use of a Basic Support. The catalyst was 10 cc of 0.7% platinum on hydrotalcite loaded into a ⅜" tube reactor heated in nitrogen (35 cc/min) to 450° C. A feedstock of di-n-propylamine (10 cc/hour) and ammonia (35 cc/min) were injected. Product was collected in a dry ice bath and the yield of liquid product was 97.2%. No cyclic materials were observed, with the major product being propionitrile formed with a selectivity of 71.6%.

What is claimed is:

1. A process for the synthesis of an azacycloheptane comprising dehydrocyclizing in the presence of a dehydrocyclization catalyst, and optionally hydrogen and/or ammonia, at dehydrocyclization conditions an amine of formula $[CH_3C(R_1R_2)C(R_3R_4)]_{2+x}NH_{(1-x)}$ where $x=0$ or 1, where each of $R_1$ and $R_2$ is independently selected from the group consisting of methyl or hydrogen, and where each of $R_3$ and $R_4$ is independently selected from the group consisting of hydrogen, methyl, or ethyl, where said dehydrocyclization catalyst is a molecular sieve in which at least 95% of the hydrogen cations are exchanged by a metal cation, said metal selected from the group consisting of the alkali, alkaline earth, lanthanide series metals, zinc, and all combinations thereof, said molecular sieve impregnated with at least one zerovalent metal selected from the group consisting of the group VIII metals iron, cobalt, nickel, ruthenium, rhodium, palladium, osmium, iridium, and platinum, and any combination thereof, and recovering the azacycloheptane produced.

2. The process of claim 1 where $R_1$, $R_2$, $R_3$ and $R_4$ are hydrogen.

3. The process of claim 1 where $R_3$ and $R_4$ are hydrogen and at least one of $R_1$ is methyl.

4. The process of claim 1 where each of $R_1$ and $R_2$ are independently selected from the group consisting of hydrogen and methyl.

5. The process of claim 1 where the molecular sieve is selected from the group consisting of zeolite L, zeolite Y, mordenite, zeolite beta, SAPO-5, SAPO-37, ALPO-5, MgAPSO-31, and MFI molecular sieves having a silica/alumina ratio of at least 20.

6. The process of claim 5 where the molecular sieve is zeolite L.

7. The process of claim 1 where at least 99% of the hydrogen cations of the molecular sieve are exchanged by a metal cation.

8. The process of claim 1 where the molecular sieve is exchanged with at least one alkali metal.

9. The process of claim 8 where the alkali metal is sodium, potassium, or any combination thereof.

10. The process of claim 1 where the molecular sieve is exchanged with at least one alkaline earth metal.

11. The process of claim 10 where the alkaline earth metal is barium, magnesium, or any combination thereof.

12. The process of claim 1 where the group VIII metal is platinum.

13. The process of claim 1 where the molecular sieve is zeolite L.

14. The process of claim 1 where the dehydrocyclization catalyst is zeolite L exchanged with at least one alkali metal and impregnated with zerovalent platinum.

15. The process of claim 1 where the dehydrocyclization conditions include a pressure from atmospheric to about 500 psig, and a temperature between about 250° and 600° C.

16. The process of claim 1 further characterized in that dehydrocyclization is performed in the presence of hydrogen.

17. The process of claim 1 further characterized in that dehydrocyclization is performed in the presence of ammonia.

* * * * *